(12) United States Patent
Bluger et al.

(10) Patent No.: US 7,085,605 B2
(45) Date of Patent: Aug. 1, 2006

(54) IMPLANTABLE MEDICAL ASSEMBLY

(75) Inventors: Henry Bluger, Victoria (CA); Jeffrey Stephen, Victoria (CA)

(73) Assignee: Epic Biosonics Inc., Saanichton (CA)

( * ) Notice: Subject to any disclaimer, the term of this patent is extended or adjusted under 35 U.S.C. 154(b) by 504 days.

(21) Appl. No.: 10/348,970

(22) Filed: Jan. 23, 2003

(65) Prior Publication Data

US 2004/0147992 A1    Jul. 29, 2004

(51) Int. Cl.
*A61N 1/04* (2006.01)

(52) U.S. Cl. .................................... 607/116

(58) Field of Classification Search ........ 607/115–156; 600/372–394
See application file for complete search history.

(56) References Cited

U.S. PATENT DOCUMENTS 5,121,754 A * 6/1992 Mullett .................. 607/117
6,374,143 B1   4/2002 Berrang

OTHER PUBLICATIONS

J. Thomas Mortimer, "Electrodes for Functional Electrical Stimulation", Final Report Contract #N01-NS-6-2346, Applied Neural Control Laboratory, Cage Western Reserve University, Cleveland OH, Aug. 2000.

* cited by examiner

*Primary Examiner*—Scott M. Getzow
(74) *Attorney, Agent, or Firm*—Paul Smith Intellectual Property Law; Paul Smith

(57) ABSTRACT

An implantable medical assembly is disclosed. The implantable medical assembly comprises at least one electrode, at least one undulated wire connected to said electrode to provide stimulation signal and a biocompatible film within which said electrode and said wire are embedded.

21 Claims, 11 Drawing Sheets

Section A-A

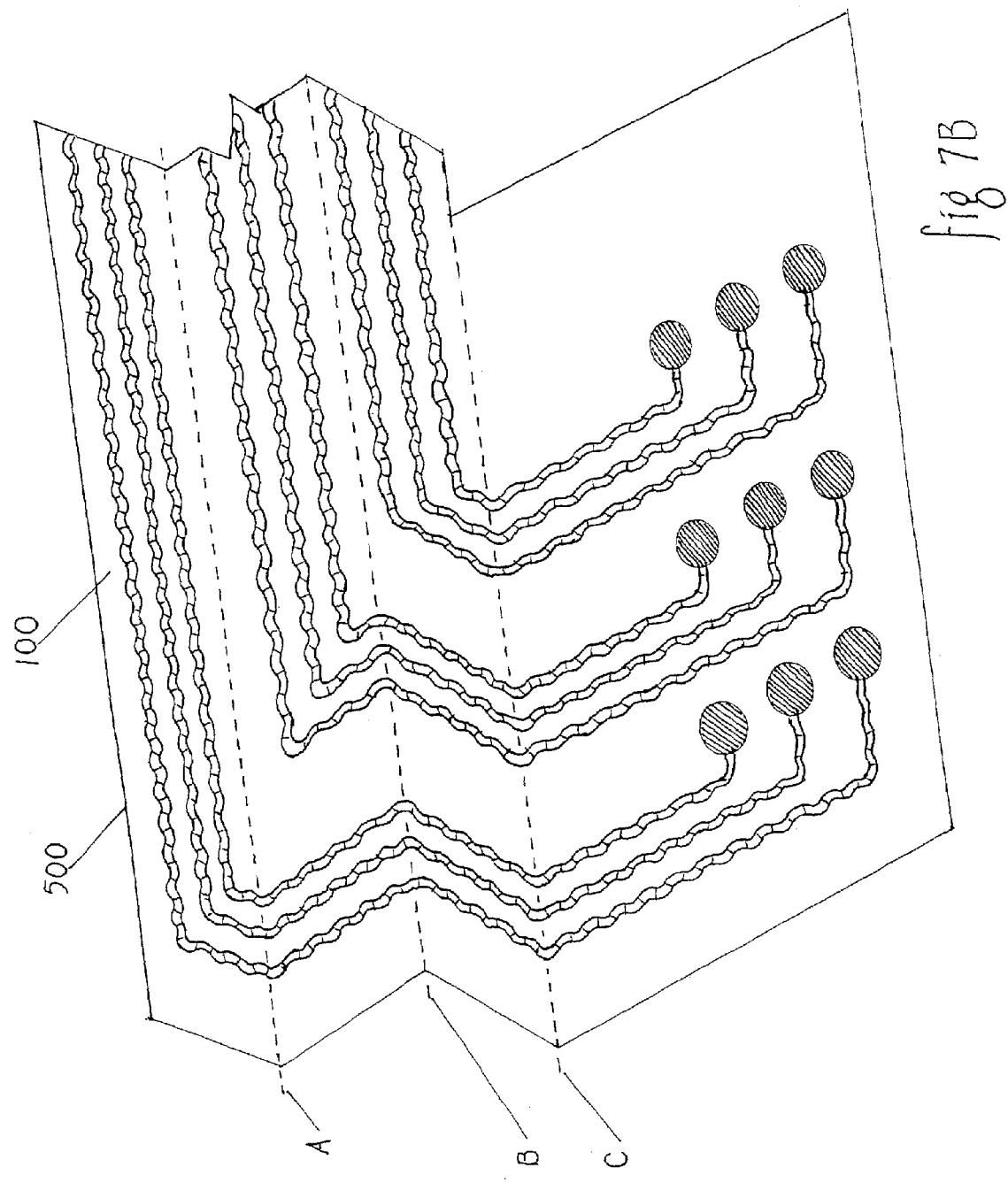

IMPLANTABLE MEDICAL ASSEMBLY

FIELD OF THE INVENTION

The present invention relates to an implantable medical assembly having a biologically compatible film within which at least one electrode and at least one conduction wire connected to the electrode to provide the stimulation signal for human nerves are embedded, and more particularly to the design of the conduction wires embedded in the biologically compatible film.

BACKGROUND OF THE INVENTION

For several years, research has been conducted in attempts to establish communication through living neurons, to convey to the human brain information which can no longer be provided by a person's own eyes or ears, to stimulate paralyzed muscles, to stimulate autonomic nerves, to control bladder function or pace the heart, or to control prosthetic limbs.

It is well known that electrical stimulation of certain nerves and certain regions of the brain can be perceived consciously, and research is being performed on methods of stimulating nerves in ways that can provide useful information to a person whose ability to hear or to see has been lost.

To replace normal sensory and motor function with a neural prosthesis, electrical communications must be made between the prosthesis and living neurons. Such connections must be made by extremely small electrodes, in order to isolate currents within small regions of living tissue. Active electrode sites can be placed very close to nerve cells, and electrical activity at the active electrode sites can be used to provide stimulation to the nerves. To limit the mechanical trauma caused by insertion and chronic presence of electrode structures, the entire electrode structure and associated conduction wires must be as small as possible consistent with the required ability to conduct electrical energy, and must be made of materials which will not react with the living body.

Implanted electrodes and the conduction wires connected to them must be electrically insulated very effectively, because of the very small voltages and currents being utilized. The localized nature of the electrical potential gradient which must be detected by a microelectrode, and the fragility of neurons, dictate a microelectrode tip with small dimensions.

Further, present neuro-stimulation devices require a large number of electrodes placed in close proximity to neural structure to facilitate effective stimulation. In addition, the neuro-stimulation devices require a hermetic electronic housing where the stimulation signals and power are generated. Because the housing is large compared to the stimulation electrodes, the package may need to be surgically placed in a location remote from the stimulation site.

It is therefore required that there be a conductor cable connecting the housing to the electrodes. With the requirement forever increasing numbers of electrodes, conduction wires with ever-increasing numbers of individual channels are needed, and thus ever increasing numbers of conduction pathways.

Because the conduction wires are located in the body, they must be made to withstand billions of micromovements to facilitate continuous operation over the long-term.

Also, conduction wires and electrodes must be constructed of bioresistive, biocompatible materials that do not cause adverse tissue reactions and that allow the structure to endure and function within the hostile electrolytic environment of the human body.

The structure of neuro-stimulation devices should also be reliably producible and relatively inexpensive to fabricate.

Implantable neuro-stimulation devices should:
 (a) be small in cross-section or small in overall size.
 (b) be fabricated from bioresistive materials.
 (c) be extremely resistant and robust under billions of micromovements of the implantee.
 (d) be supple and flexible (be able to withstand significant strains).
 (e) be able to support a large number of conductors.
 (f) maintain a reliable electrical connection between electrode and housing.
 (g) be manufacturable using reliable/economical methods of production.

To meet these demanding, requirements, a photolithographic method of fabrication has been developed.

Platinum electrodes and conduction wires can be conveniently formed using standard techniques such as laser cutting of platinum foil, chemical etching of platinum foil (see for example, R. P. Frankenthal, et. al., Journal of Electrochemical Society, 703(123), 1976).

Alternatively, a well-known photolithographic method whereby a thin coating of platinum is vacuum deposited or sputtered through a photomask, with subsequent electroplating to increase the thickness of the platinum can be used. For example, M. Sonn, et al., (Medical and Biological Engineering, pp. 778–790, November 1974) and M. Sonn (A Raytheon Company Publication PB-219 466, available from the U.S. National Information Service, U.S. Department of Commerce) used, amongst other substrates, the polyfluorocarbon FEP as a substrate onto which platinum conductors and electrodes were sputtered, with the electrode and conductor patterns defined by photolithographic etching means.

G. M. Clark, et al., (Journal of Laryngology and Otology, Vol. XC/No. 7, p623–627, 1976) describe a multi-electrode ribbon-array using a thin 0.1 µm layer of RF sputtered platinum onto FEP, subsequently insulated with FEP, and the electrode stimulating areas exposed. An array of platinum can be made to adhere to an FEP substrate insulated with additional FEP, and exposed at electrode stimulating areas. Bending tests on the array indicate that it is both flexible and strong.

H. D. Mercer, et al. (IEEE Transactions on Biomedical Engineering, Vol. BME-25, No. 6, November 1978) describes a planar lithographic technique for fabrication of a microelectrode array for a cochlear prosthesis using a sputtered platinum layer with thin molybdenum and tungsten substrates.

G. A. May, et al. (IEEE Transactions on Electron Devices, Vol. ED-26, No. 12, December 1979) describe an eight-channel tantalum-on-sapphire multielectrode array design using planar photolithography. The sapphire substrate was chosen for its electrical and mechanical properties, tantalum was applied as the conductor metal, and platinum was applied as the stimulation electrode material.

C. R. Pon, et al. (Ann. Otol. Rhinol. Largngol. 98(6) 66–71, 1989) attempted to form a standard "ring type design" electrode array by using planar photolithography to define the electrode features, RF sputtering platinum onto a polyimide substrate, rolling up the film substrate into a cylindrical shape, and filling it with medical grade silicone rubber.

J. L. Parker et al., in U.S. Pat. No. 5,720,099, describe a photolithographic technique for fabricating an elongated electrode array assembly by first depositing pads on a sacrificial layer, adding wires to the pads (such that the wires are self-supporting when the photoresist mask is removed), then embedding the wires and pads in an insulating material such as silicone elastomer, and finally removing the sacrificial layer. Importantly, a photolithographic process is used to produce the electrode assembly using a sacrificial layer as the initial base.

Those familiar with the art of photolithography and electrochemical deposition processes used in the microelectronics industry will appreciate that there are a number of well established technologies for forming micro patterns of metals and polymer encapsulation thereof.

From commonly owned which is hereby incorporated by reference, there is known an implantable electrode array which is incorporated into a neuro-stimulation device such as cochlear implant.

To better understand and appreciate the present invention, it will be helpful to briefly review an existing implantable medical assembly that is representative of other tissue-stimulating systems. An implantable medical assembly of the type currently fabricated is described in U.S. Pat. No. 6,374,143 B1.

As described in U.S. Pat. No 6,374,143 B1, and as illustrated in FIGS. 1 to 4, such existing implantable medical assembly is explained.

FIG. 1 is an implantable medical assembly having biologically compatible film within which electrodes and conduction wires are connected to the electrode to provide the stimulation signal for human nerves according to prior art. A polymer film 10 has three electrodes (1, 2 and 3) and one conduction wire 8 per electrode, disposed therein. The electrodes 1, 2, and 3 and conduction wires 8 can be fabricated from a biologically compatible and inert metal such as platinum, tantalum, rhodium, rhenium, iridium or alloys thereof, or a combination of two or more alloys and/or metal layers thereof.

The electrodes 1, 2, and 3 and the conduction wires 8 are held in place by an inert film material 10, preferentially the polyfluorocarbon FEP, although any biologically inert, high dielectric constant flexible material may be suitable. As shown in FIG. 1, each conduction wire 8 is connected to each electrode to provide a signal from the stimulator to the human nerves. Those skilled in the art will note that a myriad of possible configurations for the electrodes are possible according to neural shapes, sizes and positions.

The conduction wires 8 have an approximate width of 10–100 µm and an approximate thickness of 2–50 µm. The thickness of the encapsulating film 10 is about 20–100 µm.

Furthermore, numerous studies have been conducted to identify the biocompatibility of various implant materials (see for example "Biocompatibility of Clinical Implant Materials". Volumes 1 and 2, edited by David F. Williams, published by CRC Press, Inc., Boca Raton, Fla., USA). Some commonly used biomaterials, well known to those skilled in the art, include titanium (and some alloys thereof), platinum, tantalum, niobium, iridium, gold, some ceramics (such as alumina), certain carbon materials, some silicones, and polymers such as the fluorocarbons FEP, PTFE, PVDF, PFA, PCTFE, ECTFE, ETFE and MFA (a copolymer of TFE and PVE), polyethylene's, polypropylenes, polyamides and polyimides.

FIG. 2 is a cross-sectional view of section 'A—A' of FIG. 1 showing some embedded metal electrodes and conduction wires. The electrode 1 is exposed to the human nerves to transfer the stimulation signals from the conductor 8.

FIG. 3 is a planar view to illustrate where to fold-in and fold-out an implantable medical assembly according to prior art. FIG. 4 is a perspective view showing the film being folded over along the folding-in and folding-out lines L1, L2 and L3. To make a suitable shape and size for a neural stimulation implant assembly 10 such as a cochlear implant, the implantable medical assembly needs to be folded along the virtual in-folding and out-folding lines L1, L2 and L3 established by the manufacturer.

These lines L1, L2 and L3 are not actually marked on the film 10 in the prior art. When folding the medical assembly, careful handling of the assembly is required. For example, one stimulation implant may need to incorporate multiple folds or more without impairing the structure of the implantable medical assembly.

In prior art shown from FIG. 1 to FIG. 4, the conduction wires 8 having a straight shape are easily fractured because of the continuous movement of the tissues of the body following implantation. This can cause severe problems for the implantee.

The implantable medical assembly requires discrete electrical continuity of the individual conduction wires. Also, electrodes should be maintained to ensure proper signal transfer between target nerves and the implant housing wherein electronic circuits to control the nerves reside. If only one conduction wire is fractured, partial or total malfunction of the implant may result.

SUMMARY OF THE INVENTION

In view of the above-mentioned disadvantages of the prior art, it is an objective of the present invention to provide an implantable medical assembly for various rehabilitation systems such as cochlear implants.

A still further objective of the invention is to provide an implantable medical assembly which can be reliably implanted with long term stability.

Yet a further objective is to provide an implantable medical assembly which has more stable mechanical and electrical characteristics.

In a view of the foregoing, another objective of the present invention is to provide an implantable medical assembly which has improved tensile properties (i.e. stretchable without failure) compared to the prior art structure (straight wiring).

A yet further objective of the present invention is to provide an implantable medical assembly which is easier to manufacture.

A yet further objective of the present invention is to increase the redundancy of conduction wires on an implantable medical assembly, to ensure the electrical functionality of the implant even though one or more of the conduction wires may be fractured.

A yet further objective of the present invention is to increase the strength of the signal cable that connects an implant with its stimulator.

In accordance with the present invention, an implantable medical assembly comprises a biologically compatible film, at least one electrode on the film, and at least one wire on the film being connected to the electrode to provide a stimulation signal, wherein the wires have a photolithographically defined undulated shape.

In the present invention, first, on the substrate, the electrodes and the conductor wires made of platinum or other noble metal are deposited through electro deposition process. Then, the first FEP film is laminated to cover all the substrate including the electrodes and the conductors. Next the substrate is removed, and then other FEP film is deposited to cover the remained structure using a heated press, and then the electrodes and the conductor wires are embedded within FEP film. Then, the electrodes can be exposed as shown in FIG. 2. This whole process may be performed through photolithography method using already mentioned prior art.

Preferably, in accordance with the present invention, an implantable medical assembly comprises a biologically compatible film, at least one electrode within the film, at least two wires within the film being connected to the same electrode to provide a stimulation signal, wherein the wires carry the same stimulation signal. In the implantable medical assembly, the two wires come from one wire having a single stimulation signal. The wires have an undulated shape and at least one electrical connector forms an electrical link between the two wires.

Preferably, in accordance with the present invention, an implantable medical assembly comprises a biologically compatible film, at least one electrode within the film, at least one wire within the film and being connected to the electrode to provide a stimulation signal, and at least one folding line on the film for folding. In the implantable medical assembly, the wire has an undulated shape. The folding line has a plurality of holes or cut-outs on the film. Further, the medical assembly is folded according to the folding line(s), is then corrugated, and finally encased within an elastomer such as a silicone.

As already mentioned, this invention utilizes the photolithographic technology. To produce a narrow cable containing a large number of conduction wires requires that the wires be spaced very close together. According to one development of the invention, the process for building up multiple layers to incorporate a large number of conductors into a narrow thin cable is proposed. In this invention, a very thin film having a large surface area containing conduction wires and electrodes is folded into a very narrow diameter cable with a large number of wires.

The folding technique makes it possible to reduce a very broad medical implant system into a fine and narrow cable system. According to the present invention, the conduction wires are undulated to impart longitudinal strain resistance. With a broader area, multiple conductors for each channel add redundancy to the system.

Further, the wires can be laddered to enhance the conveyance of stimulation signals in case of fracture at points along the wires. For easy folding of the implantable medical assembly, cuts or holes can be marked on the FEP film to guide and control the location of these folds. The folded structure can be undulated to allow further strain resistance. The undulated structure can be encapsulated in elastomer such as silicone.

The reduced stresses on the conduction wires allow the wires to be made from less-than-ideal materials. That is, they can be made from the same materials as the electrodes, which, generally, do not have ideal mechanical properties. The implication is that the electrodes and wires are one contiguous material without the reliability problems associated with connecting different metals together, and without the electrolytic corrosion problems that occur when dissimilar metals are in an electrolytic environment for extended periods.

BRIEF DESCRIPTION OF THE DRAWINGS

FIG. 7B shows a perspective view of the film being folded over along the folding-in and folding-out lines.

DETAILED DESCRIPTION OF THE PREFERRED AND ALTERNATIVE EMBODIMENTS OF THE INVENTION

The following describes the best mode presently contemplated for carrying out the invention. This description is not to be taken in a limiting sense, but is made merely for describing the general principles of the invention. The scope of the invention should be determined with reference to the claims.

Figure 5:
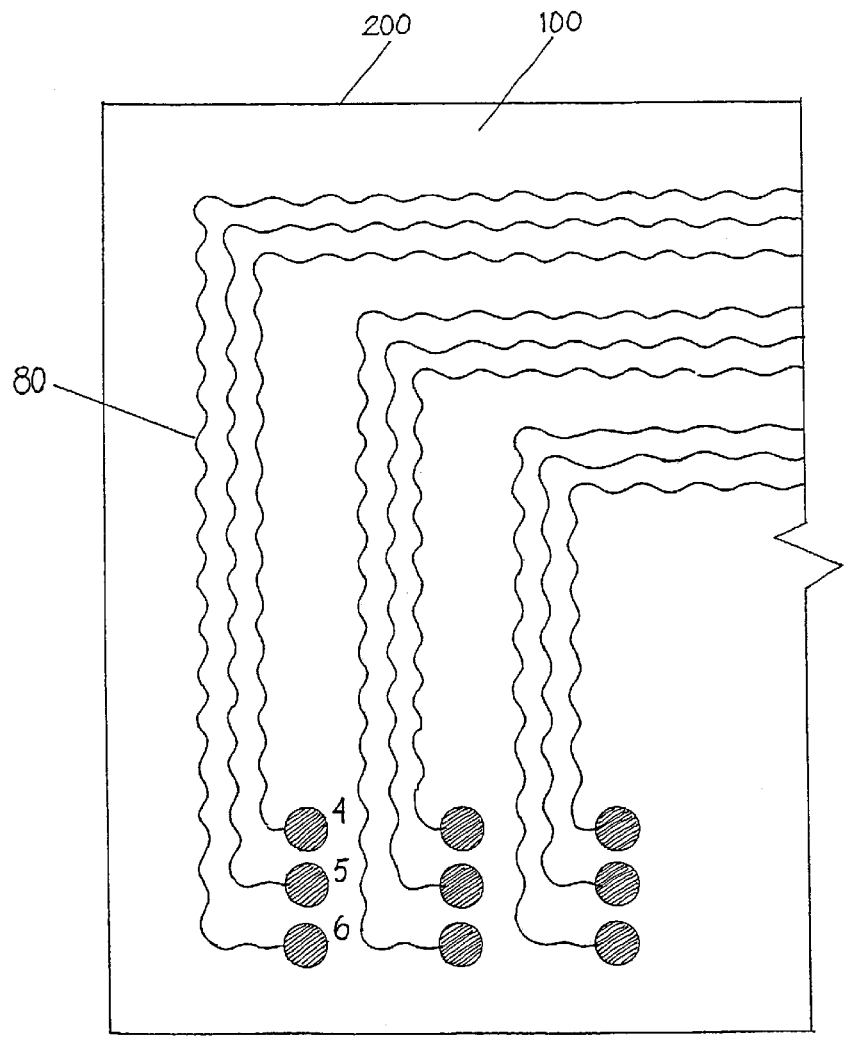
FIG. 5 shows a planar view of a preferred embodiment of an implantable medical assembly with undulated wires according to the present invention.

FIG. 5 shows a planar view of a preferred embodiment of an implantable medical assembly with undulated conduction wires according to the present invention. The aforementioned implantable medical assembly is designed to carry electrical signals from the housing that contains the electrical stimulator to the electrodes of an implantable nerve stimulation device for the purpose of safely and reliably stimulating human nerves. According to an implantable medical assembly 200 shown in FIG. 5, conduction wires 80 with an undulated structure are connected to electrodes 4, 5 and 6 and embedded within a suitable biocompatible material 100, such as FEP film. The bonding between the conduction wires 80 and FEP film 100 will be maintained while the implantable medical assembly 200 is exposed to body fluids and minor body temperature fluctuation cycles. Undulated conduction wires 80 and electrodes 4, 5, and 6 are formed using well-known photolithographic and electrochemical deposition processes and encapsulated within biocompatible material using established polymer encapsulation techniques.

Figure 1:
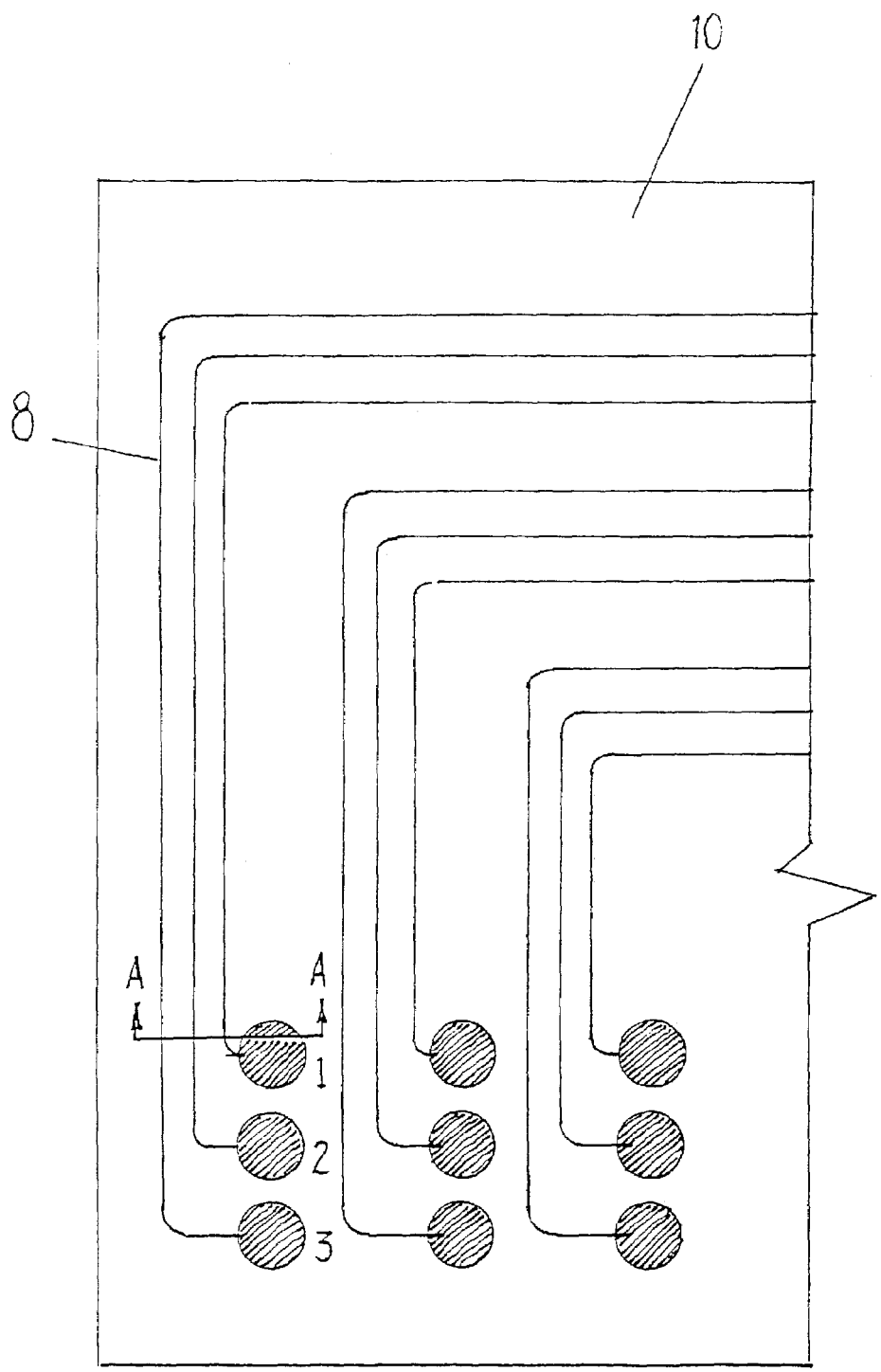
FIG. 1 is a planar view of an implantable medical assembly having biologically compatible film within which electrodes and conduction wires, connected to the electrodes, provide stimulation signals to human nerves according to prior art.
Figure 2:
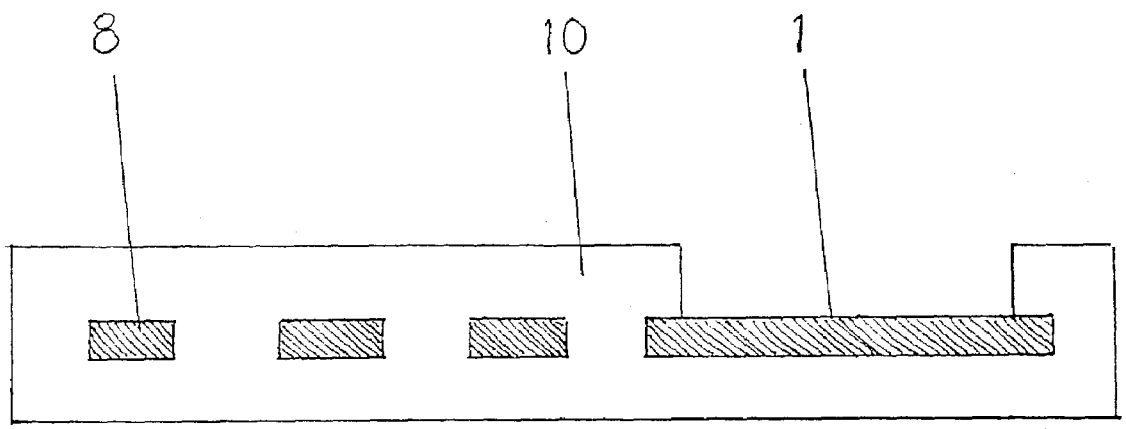
FIG. 2 is a cross-sectional view of section 'A—A' of FIG. 1 showing some embedded metal electrodes and conduction wires according to FIG. 1.
Figure 3:
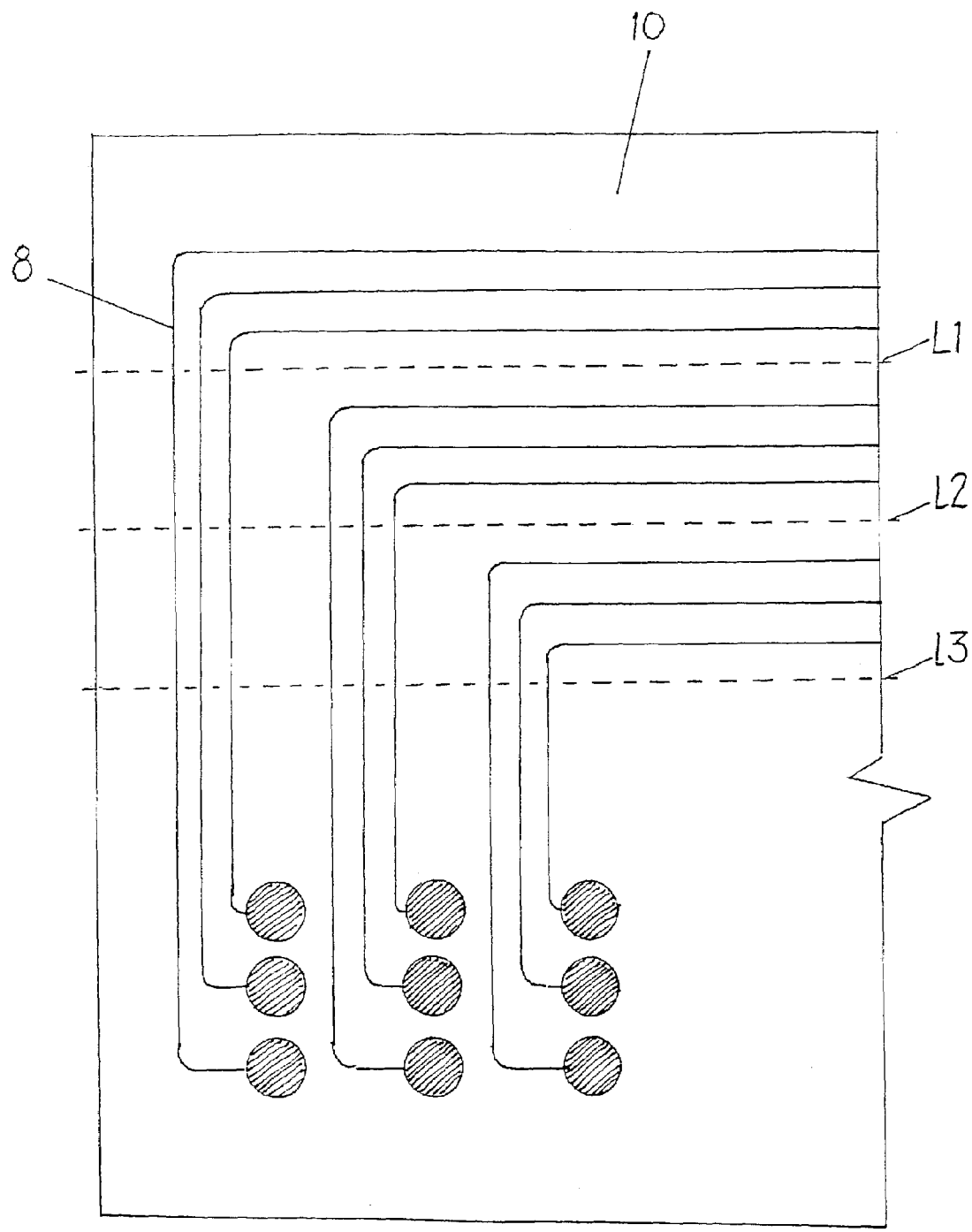
FIG. 3 is a planar view illustrating how where to fold-in and fold-out an implantable medical assembly according to prior art.
Figure 4:
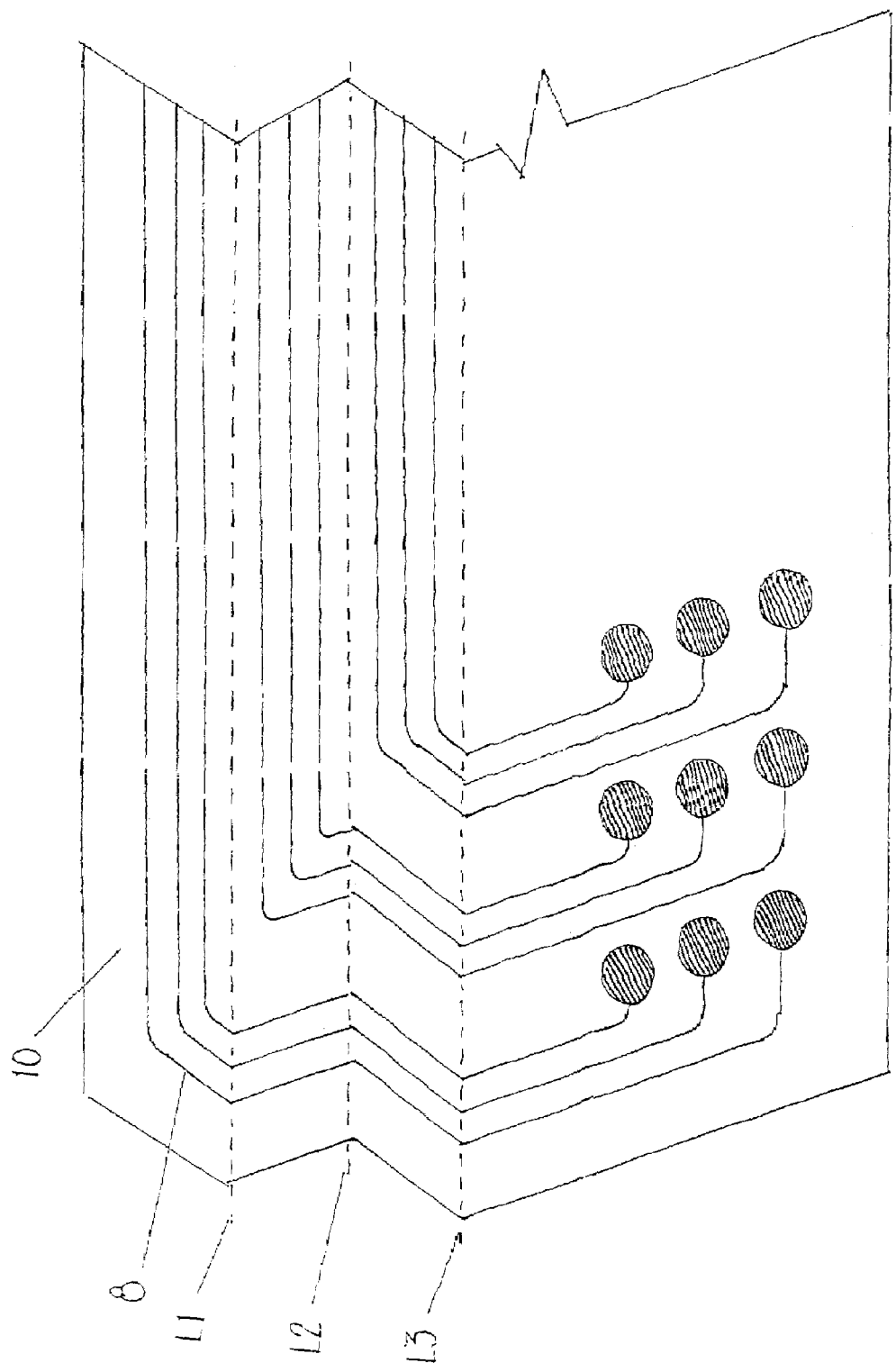
FIG. 4 is a perspective view showing the film being folded over along the fold-in and fold-out lines.

The conduction wires 80 with undulated shape are embedded within FEP film 100 to increase the ability of overall implantable medical assembly 200 to undergo strain. The undulated shape of the wires 80 allows the implantable medical assembly 200 to be stretched without damage to the conduction wires since the stress acting upon the implantable medical assembly 200 is carried both by the undulated conduction wires 80 and the FEP film 100. The undulated shape of the conduction wires 80 allows stretchability, elasticity of the implantable medical assembly 200 according to the present invention. Compared to the prior art structure shown in FIG. 1 (straight wiring), the tensile strength of the present invention is greatly improved, thereby enhancing reliability and safety of the implantable device.

Figure 6A:
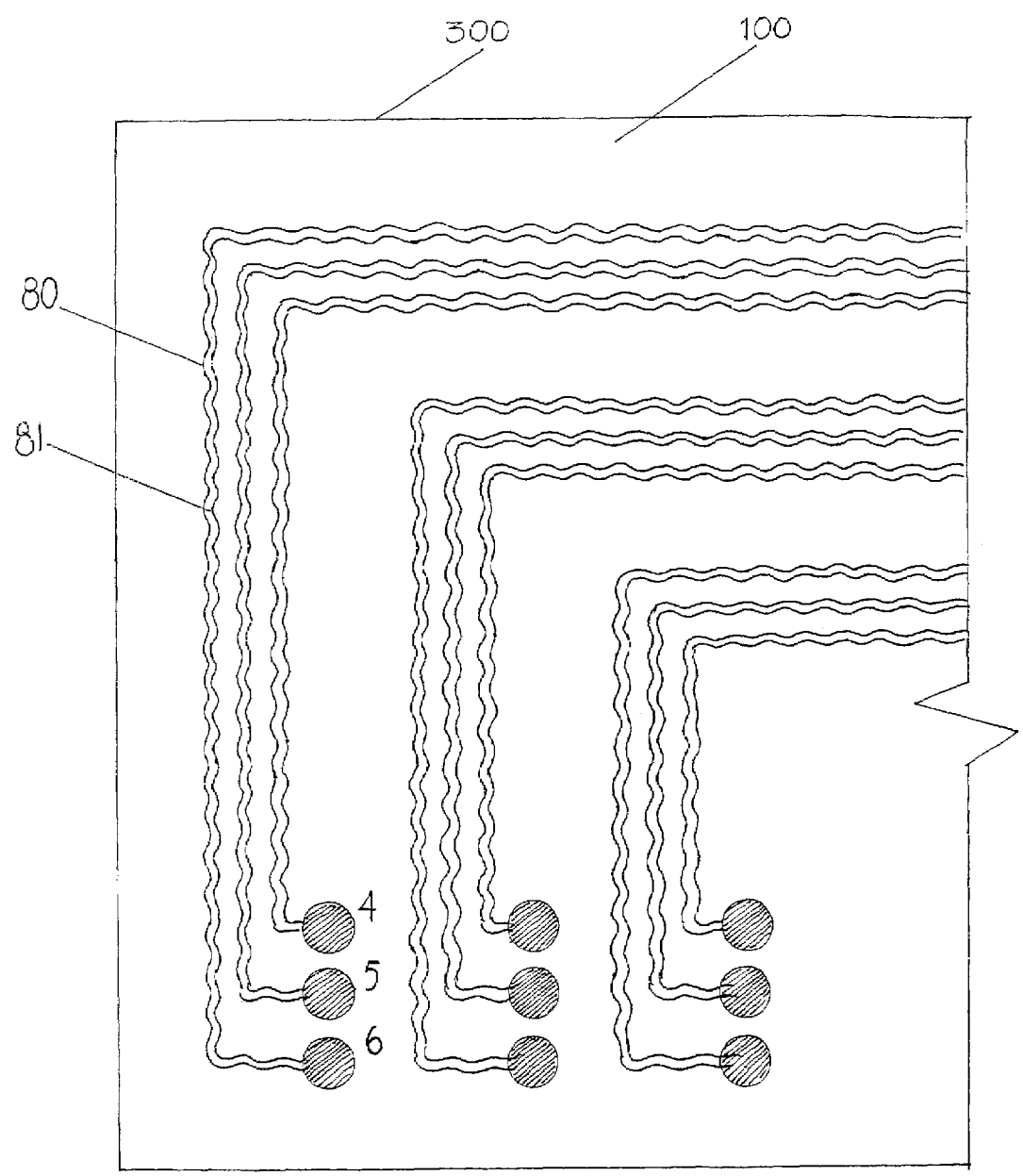
FIG. 6A shows a planar view in a further embodiment with multiple conduction wires to one electrode according the present invention.

FIG. 6A shows a planar view in a further embodiment of an implantable medical assembly 300 with multiple conduction wires 80 and 81 connected to one electrode 6 according the present invention. To increase the reliability of the conduction wires conveying stimulation signals from a stimulator (not shown), a plurality of conduction wires having the same signals are connected to one electrode. These conduction wires may be branched off one conduction wire. As shown in FIG. 6A, electrodes 4, 5 and 6 are connected with two conduction wires 80 and 81. Two undulated conduction wires 80 and 81 convey the same signals, thereby ensuring signal conveyance even if one conduction wire is fractured by movements within the body of the implantee. To increase the overall redundancy of the conduction wires, more than two conduction wires having the same stimulation signals may be connected to each electrode.

Figure 6B:
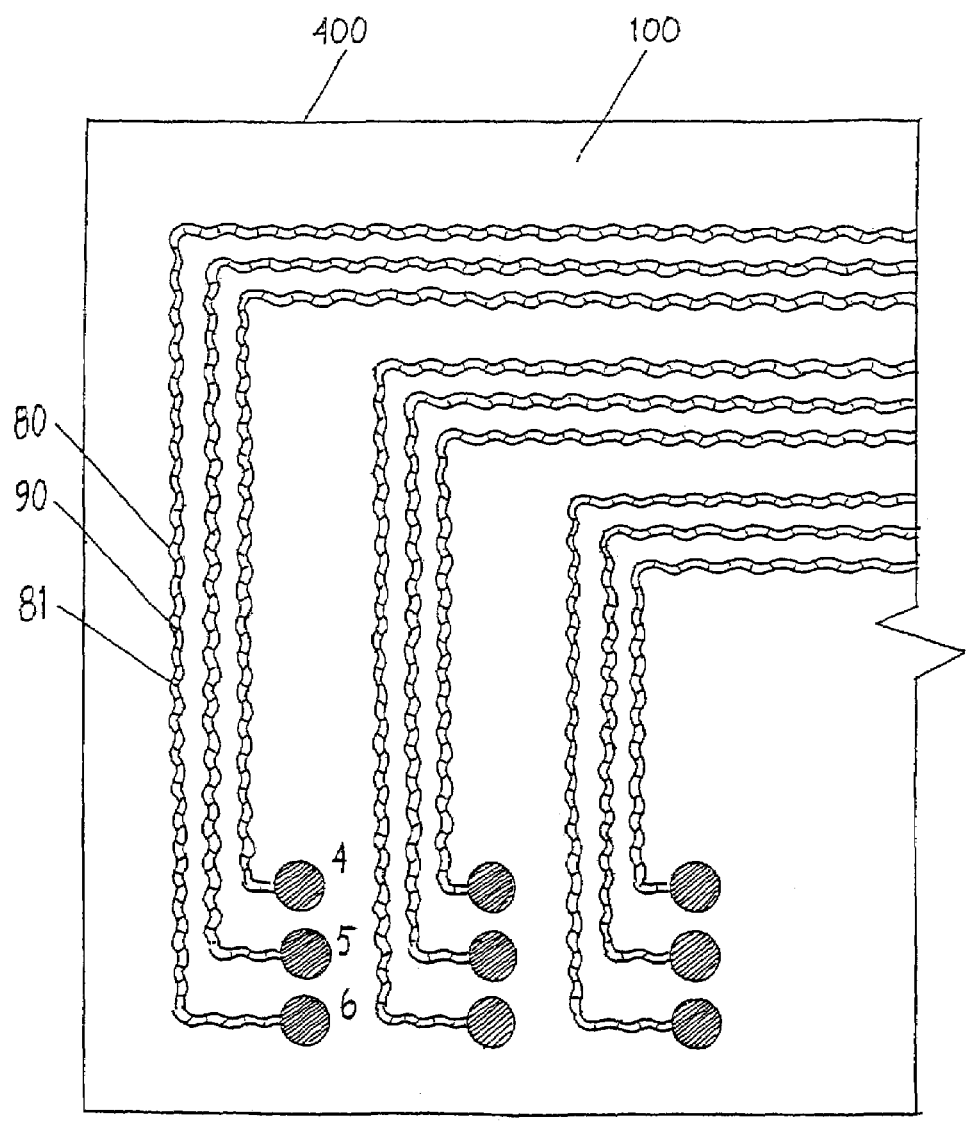
FIG. 6B shows a planar view of a further embodiment of a related embodiment of an implantable medical assembly with multiple electrical connectors between conduction wires according to the present invention.

FIG. 6B shows a further embodiment of an implantable medical assembly 400 with multiple electrical connectors 90 disposed between conduction wires according to the present invention. That is, two or more conduction wires which are connected to the same electrode are laddered, thereby further ensuring the signal conveyance. These electrical connectors 90 are complementarily connected between pairs of conduction wires 80 and 81 to deliver the stimulation signal even if one of the conduction wires is fractured in more than one location because of the movement of body tissues or from other various causes such as manufacturing or damage during implantation. This structure assures conveyance of the stimulation signal from a stimulator (not shown) to electrodes 4, 5 or 6. The electrical connectors 90 may be composed of the same material, such as platinum, as the conduction wires 80 and 81. Preferably, the material of the electrical connectors 90 is the same material as the conduction wires 80 and 81. However, other materials, which are compatible with the material of the conduction wires 80 and 81, are also possible.

Figure 7A:
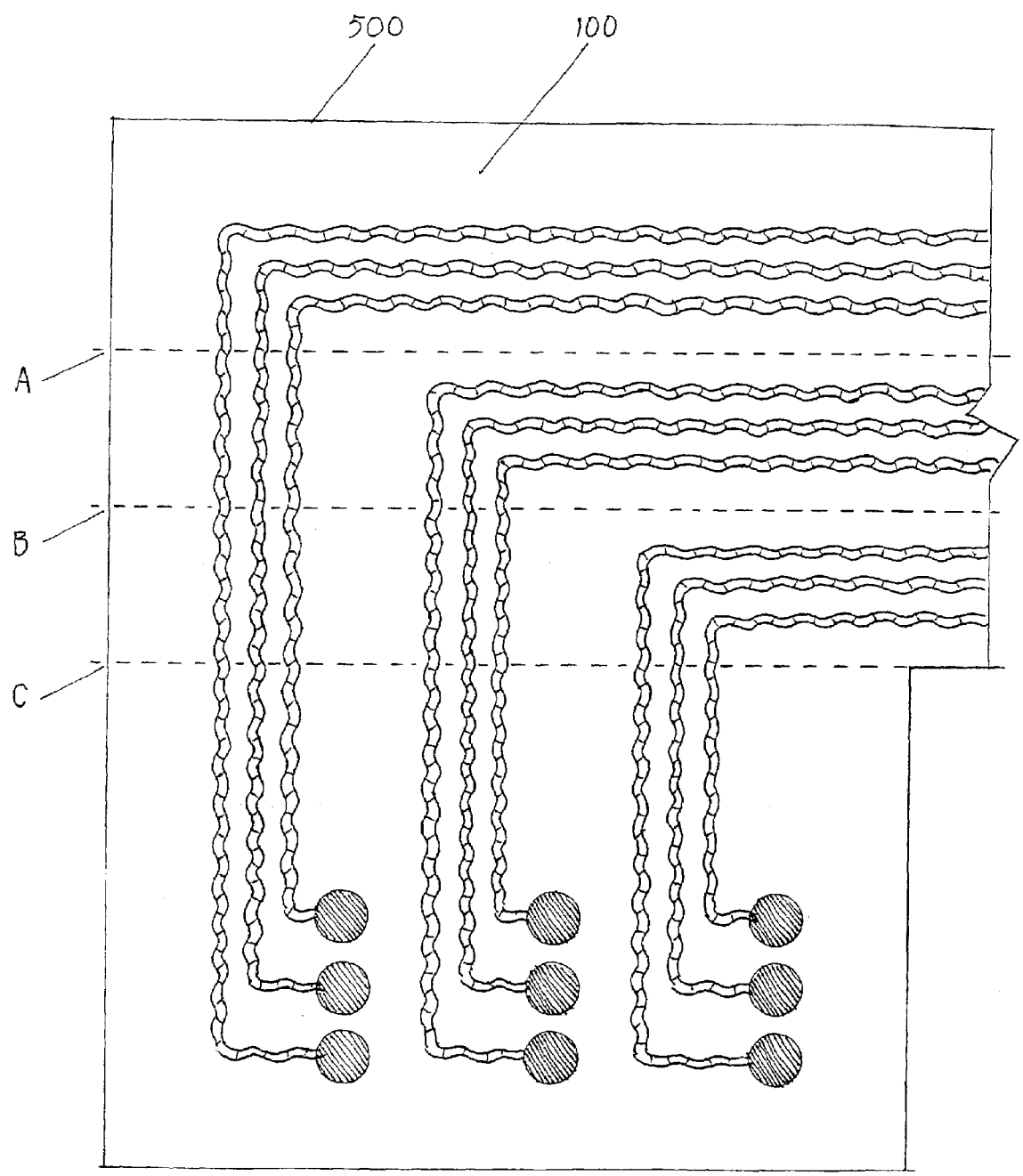
FIG. 7A shows a planar view of a further embodiment of an implantable medical assembly having folding marks along the folding lines of an implantable medical assembly according to the present invention.

FIG. 7A shows a planar view of a further embodiment of an implantable medical assembly 500 having folding marks along the folding lines A, B and C of the implantable medical assembly according to the present invention. FIG. 7B shows a perspective view showing the film being folded over along the folding-in and folding-out lines. The folding lines A, B, and C facilitate the folding operation when folding the implantable medical assembly 500. Each folding line consists of fine holes or cuts shaped by a process such as laser cutting. During the manufacturing process, the medical assembly 500 is folded to create an electrical lead for the final implantable device such as cochlear implant or other implantable nerve stimulating device. According to the design and size of the medical device, the implantable medical assembly 500 is folded a number of times to create a suitable electrical lead for the implantable device.

Figure 8A:
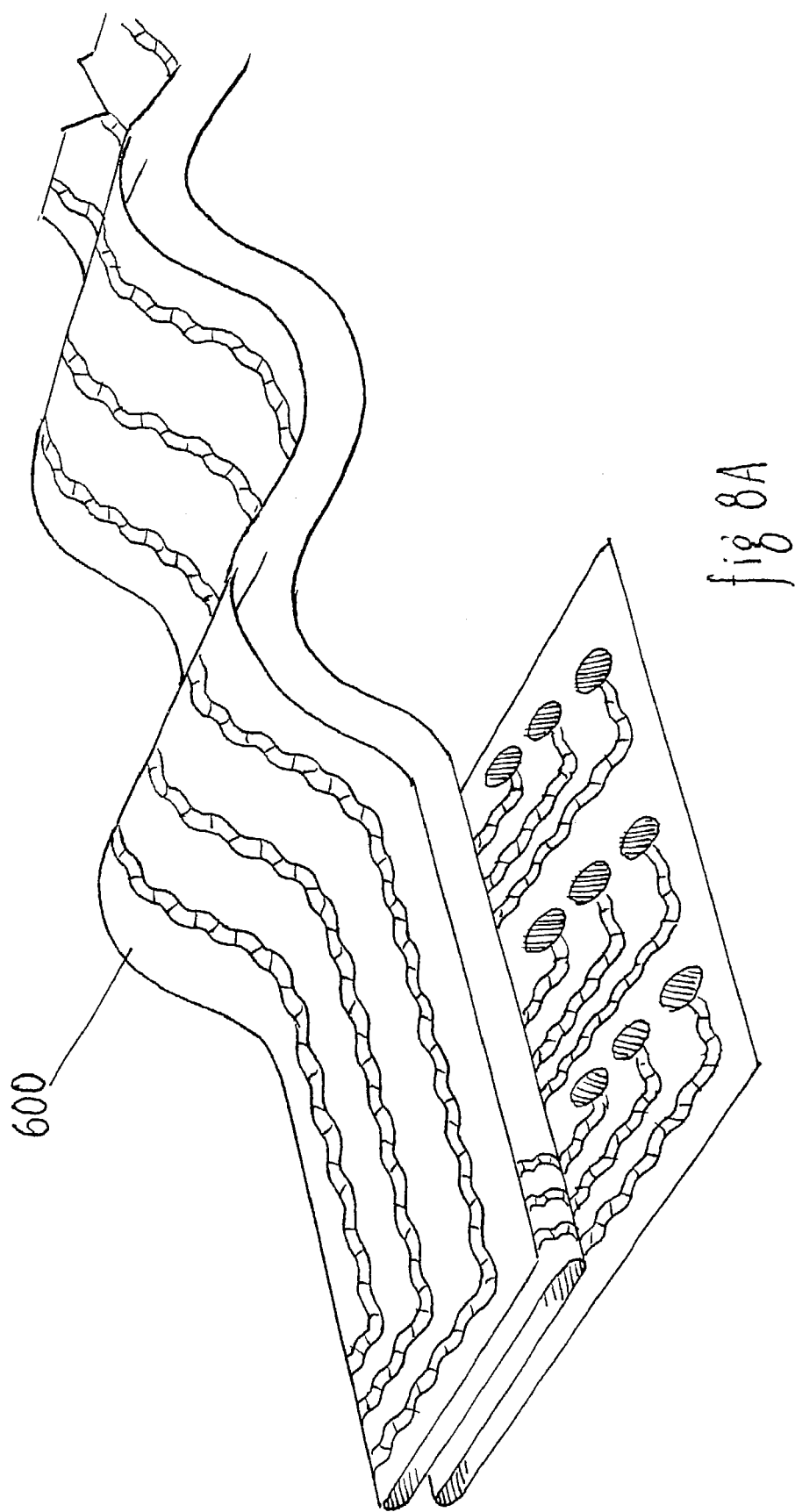
FIG. 8A shows a schematic view of the implantable medical device having an overall corrugated shape according to the present invention.

FIG. 8A shows a perspective view of the implantable medical assembly 600 having an overall corrugated shape according to the present invention. This assembly may be applied to a cochlear implant or other nerve stimulating implant. Further, this assembly may be applied to the connection cable between the implantable medical assembly and the stimulator. To increase the expandability and elasticity of the implantable medical assembly 500 after predetermined folding, the implantable medical assembly is molded to have the corrugated shape 600. Therefore, the implantable medical assembly 600 can readily be expanded or contracted.

Figure 8B:
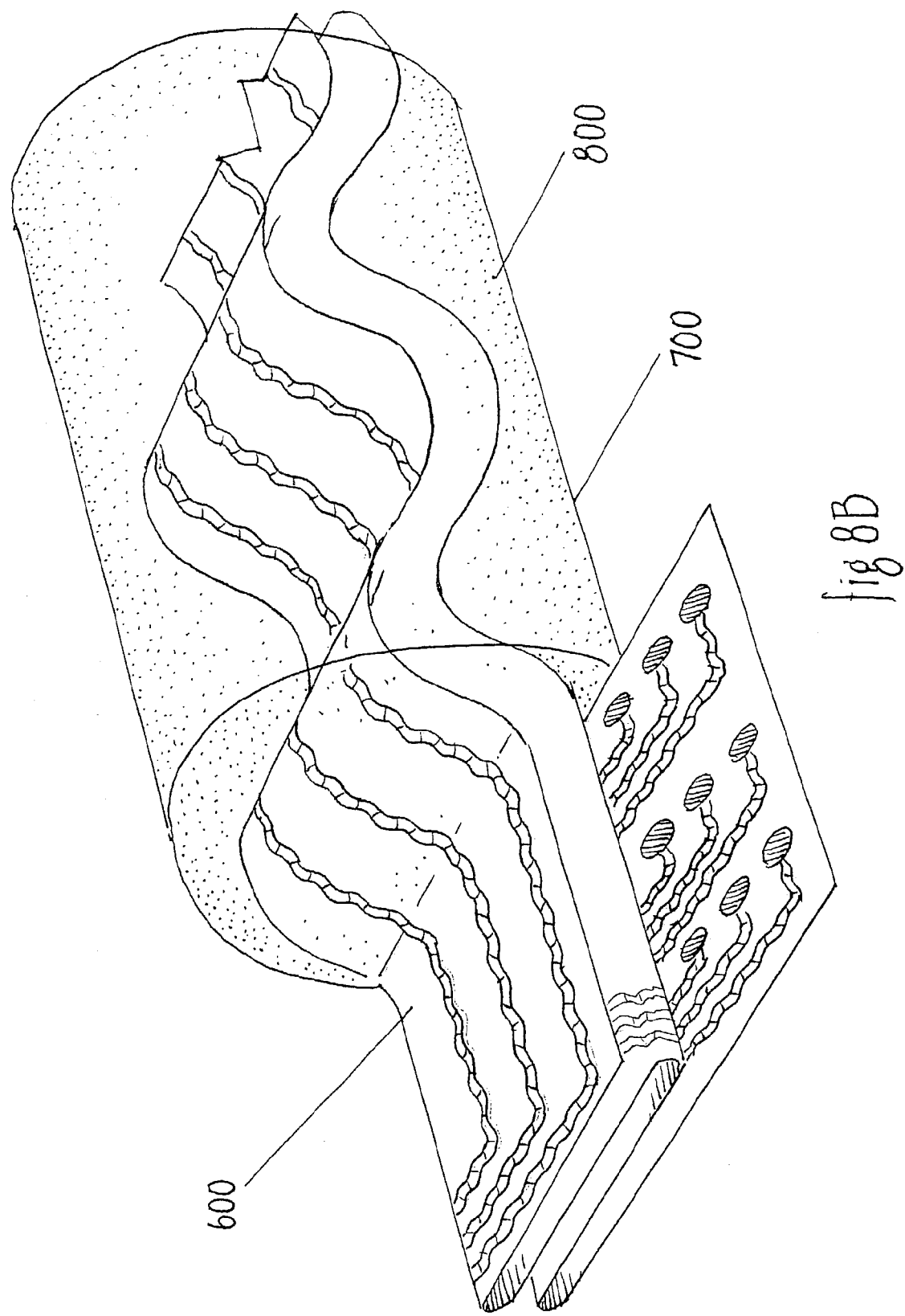
FIG. 8B shows a schematic view of the implantable medical device having an overall corrugated shape encased with elastomer such as silicone according to the present invention.

FIG. 8B shows a perspective view of the implantable medical assembly having an overall corrugated shape encased with elastomer such as silicone according to the present invention. The implantable medical assembly 600 is encased with a biocompatible elastomer 800 such as silicone to protect the overall implantable medical assembly 700 according to the present invention.

The present invention may be applied to the electrical connection (lead or cable) between implantable housings or medical devices in which electronic circuits reside. That is, in any implantable medical device designed to deliver or receive electrical signals, the present invention ensures safe and reliable delivery or reception of those electrical signals. Further, this implantable medical assembly can be applied to the electrical connection between an implantable housing and an implantable antenna for RF communication used in an implantable medical device.

Moreover, as described above, it is seen that the implantable medical assembly described herein may be manufactured using low cost technology and simple-to-implement manufacturing techniques for mass production.

Finally, it is seen that the implantable medical assembly of the present invention may be safely and reliably used in various nerve stimulation assemblies.

The above descriptions are intended to illustrate the preferred and alternative embodiments of the invention. It will be appreciated that modifications and adaptations to such embodiments may be practiced without departing from the scope of the invention, such scope being most properly defined by reference to this specification as a whole and to the following claims.

What is claimed is:

1. An implantable medical assembly comprising:
    at least one electrode;
    at least one undulated wire connected to said electrode to provide a stimulation signal, wherein said wire and said electrode are together photolithographically patterned and electrochemically deposited;
    and a planar biocompatible film within which said electrode and said wire are embedded;
    wherein said assembly is corrugated.

2. The implantable medical assembly of claim 1 wherein said assembly is corrugated after folding.

3. The implantable medical assembly of claim 2 wherein said medical assembly is encased with an elastomer such as a silicone.

4. An implantable medical assembly comprising:
    at least one electrode;
    at least two wires commonly connected to each said electrode to provide stimulation signals, wherein said wires and said electrode are together photolithographically patterned and electrochemically deposited;

and a planar biocompatible film within which said electrode and said wires are embedded.

5. An implantable medical assembly of claim 4 wherein at least one electrical connector is connected between said wires.

6. The implantable medical assembly of claim 4 or 5 wherein said assembly is corrugated.

7. The implantable medical assembly of claim 4 or 5 wherein said assembly is corrugated after folding.

8. The implantable medical assembly of claim 7 wherein said medical assembly is encased wit an elastomer such as a silicone.

9. An implantable medical assembly comprising:
at least one electrode;
at least two undulated wires having the same stimulation signals and connected to each said electrode to provide stimulation signals, wherein said wires and said electrode are together photolithographically patterned and electrochemically deposited;
and a planar biocompatible film within which said electrode and said wires are embedded.

10. An implantable medical assembly of claim 9 wherein at least one electrical connector is connected between said wires.

11. The implantable medical assembly of claim 9 or 10 wherein said assembly is corrugated.

12. The implantable medical assembly of claim 9 or 10 wherein said assembly is corrugated after predetermined folding.

13. The implantable medical assembly of claim 12 wherein said medical assembly is encased wit elastomer such as a silicone.

14. The implantable medical assembly of claim 4 or 5 or 10, or 11 wherein said implantable medical assembly further comprises at least one folding line on said film.

15. The implantable medical assembly of claim 14 wherein said implantable medical assembly is corrugated.

16. The implantable medical assembly of claim 14 wherein said implantable medical assembly is corrugated after folding.

17. The implantable medical assembly of claim 16 wherein said medical assembly is encased with elastomer such as a silicone.

18. An implantable medical assembly comprising:
at least one electrode;
at least one undulated wire connected to said electrode to provide a stimulation signal, wherein said wire and said electrode are together photolithographically patterned and electrochemically deposited;
and a planar biocompatible film within which said electrode and said wire are embedded;
wherein said implantable medical assembly further comprises at least one folding line on said film.

19. The implantable medical assembly of claim 18 wherein said implantable medical assembly is corrugated.

20. The implantable medical assembly of claim 18 wherein said implantable medical assembly is corrugated after folding.

21. The implantable medical assembly of claim 20 wherein said medical assembly is encased with elastomer such as a silicone.

* * * * *

UNITED STATES PATENT AND TRADEMARK OFFICE
CERTIFICATE OF CORRECTION

| | | |
|---|---|---|
| PATENT NO. | : 7,085,605 B2 | Page 1 of 1 |
| APPLICATION NO. | : 10/348970 | |
| DATED | : August 1, 2006 | |
| INVENTOR(S) | : Henry Bluger and Jeffrey Stephen | |

It is certified that error appears in the above-identified patent and that said Letters Patent is hereby corrected as shown below:

Column 9, line 11, replace "wit" with --with--.
Column 9, line 31, replace "wit" with --with--.
Column 10, line 2, replace "10, or 11" with --9 or 10--.

Signed and Sealed this

Twenty-sixth Day of December, 2006

JON W. DUDAS
*Director of the United States Patent and Trademark Office*